United States Patent [19]
Tolkoff

[11] Patent Number: 4,654,036
[45] Date of Patent: Mar. 31, 1987

[54] ELONGATED WEIGHTED MEDICAL DEVICE

[75] Inventor: Marc J. Tolkoff, Brookline, Mass.

[73] Assignee: Norwich-Eaton Pharmaceuticals, Inc., Ohio

[21] Appl. No.: 820,878

[22] Filed: Jan. 16, 1986

Related U.S. Application Data

[63] Continuation of Ser. No. 680,596, Dec. 11, 1983, abandoned, which is a continuation of Ser. No. 374,264, May 3, 1982, abandoned.

[51] Int. Cl.[4] .............................................. A61M 25/00
[52] U.S. Cl. ...................................... 604/270; 604/27
[58] Field of Search ................ 604/27, 270, 280, 281, 604/282

[56] References Cited

U.S. PATENT DOCUMENTS

| | | | |
|---|---|---|---|
| 1,736,182 | 11/1929 | Wilkins | 604/270 |
| 3,421,499 | 1/1969 | Bray et al. | 604/270 X |
| 3,941,119 | 3/1976 | Corrales | 604/270 X |
| 4,052,989 | 10/1977 | Kline | 604/282 X |
| 4,410,320 | 10/1983 | Dykstra | 604/27 |

*Primary Examiner*—Edward M. Coven

[57] ABSTRACT

An elongated rod-shaped medical device has a weighted portion of greater density than adjacent portions thereof for providing useful weight in light medical devices. The weighted portion has a plurality of interfitting metallic weights with facing, engaging sliding surfaces to provide for high specific gravity and high bulk density in a yieldable small diameter device.

3 Claims, 2 Drawing Figures

ELONGATED WEIGHTED MEDICAL DEVICE

This is a continuation of application Ser. No. 680,596, filed Dec. 11, 1983, now abandoned, which is a continuation of application Ser. No. 374,264, filed May 3, 1982, now abandoned.

BACKGROUND OF THE INVENTION

A variety of medical devices require weighted portions to provide pulling weights acted on by gravity to straighten, position, move and handle the devices. Such devices include weighted feeding tubes for the body, gastric tubes and the like which are passed into the body, with weights aiding in advancing the lightweight small diameter devices through body passageways employing the force of gravity. Generally, it is preferred that such devices be flexible and of small diameter. They often are formed of plastic or rubber and require dense and heavier portions than the plastic or rubber without significant increase in overall diameter. Significant increase in diameter could make the devices more difficult to use and to pass through the body orifices and channels.

The prior art has often used liquid metals, typically mercury, for the denser portion. The one advantage of liquid mercury is that it enables catheters to remain flexible since liquid is yieldable. Additional weight is provided because of the high specific gravity (13.6) of mercury. Mercury has certain disadvantages which include its toxicity which is of particular concern in medical devices. Moreover, its weight is limited and it is sometimes desirable to provide a higher bulk density for a required weight so as to conserve space taken up by the weight.

SUMMARY OF THE INVENTION

According to the invention an elongated rod-shaped medical device is provided with interfitting metallic weights of solid metals having high specific gravity and high bulk density with a plurality of such weights enabling yielding of medical devices when necessary.

Another object of this invention is to provide a weighted medical device in accordance with the preceding object which is non-toxic, yielding under hand pressure, conformable to body contours and provides sufficient weight in small areas as may be necessary.

Still another object of this invention is to provide a method of weighting an elongated rod-shaped medical device to provide high specific gravity and high bulk density in a portion of that device where required.

According to the invention an elongated rod-shaped medical device for use in the human body has a weighted portion of greater density than adjacent portions thereof. The weighted portion has a plurality of interfitting metallic weights. The weights have engaging, sliding surfaces adjacent to each other to provide for a high specific gravity section with high bulk density. The rod-shaped devices can be catheters, feeding tubes and the like having an outer diameter preferably no more than about one-half inch. The weighted portion is capable of yielding under hand pressure and forces encountered in the body so as to be conformable to bends and contortions of the body cavities and passageways encountered in use. Preferably the weighted portion is substantially contained within the rod outer diameter and the rod outer diameter comprises a resilient, yieldable polymeric hydrocarbon material. Preferably the metal has a specific gravity higher than 13.6 and the weighted segment has a bulk density of 70 or greater. This is provided by using heavy metals preferably in the form of side by side mating seriatim arranged metallic disks.

It is a feature of this invention that the metals used can be non-toxic eliminating the prior art dependency on toxic mercury. The catheters and devices with which the weights are used can be formed of flexible materials and the disks do not substantially decrease flexibility. Greater weight is provided in the same volume by using metal with high specific gravity. The weights are safe both in form as well as chemical composition. Handling the disks in both use of catheters and manufacture of catheters, is easier and safer than the handling of toxic mercury weights.

The solid metal disks are preferably short so that the plastic or rubber tube which contains them can flex easily in the same manner as if filled with mercury.

BRIEF DESCRIPTION OF THE DRAWINGS

The above and other objects, features and advantages of the present invention will be better understood from a reading of the following specification in conjunction with the drawings in which.

DESCRIPTION OF PREFERRED EMBODIMENTS

Figure 1:
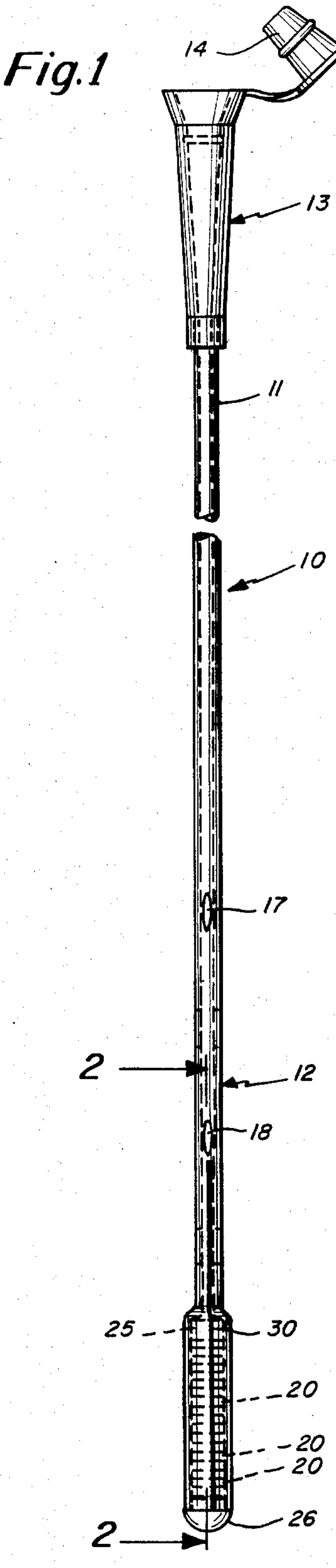
FIG. 1 is a side view of a feeding tube in accordance with the present invention.

With reference now to the drawing and more particularly FIG. 1, a feeding tube 10 is illustrated comprising a body tube section 11, a weighted distal end section 12 and a proximal cap or fitting end 13.

The feeding tube 10 is the illustrative device shown in this application. However, the medical device to be weighted can be any of the commonly weighted medical devices or others as for example feeding tubes, gastric tubes, catheters of various types and the like. In all cases, they are elongated rod-shaped medical devices and have relatively low specific gravities since they are often formed of body tubes 11 of organic hydrocarbon resins. Preferably materials such as silicone rubber, other natural or synthetic rubber, polyvinylchloride, polypropylene and like materials are used. In all cases, it is preferred that the materials be flexible and resilient having sufficient body to enable passage into the human or mammalian body during normal handling. While tubes are normally used having central passageways as for withdrawal or introduction of fluids and the like, in some cases, the medical devices can be solid elongated bodies. The overall shape is preferably round as in the preferred embodiment but oval and other cross section rod-like devices can be used.

The end 13 can be of any type. It is the end that remains outside the body and in the present invention, comprises end caps 14 and fitting which can be sealed. End cap 14 can be used to close a body entrance for fluids and the like and can cover a luer lock fitting for attachment of a syringe.

A plurality of oval openings 17 and 18 are provided at the distal end of the device to enable fluids to be passed into and taken from the body cavity into which the feeding tube is placed. The length of the tube can vary greatly as can the diameter although in all cases, it is preferred that the diameter be no more than about one-half inch. In normal cases, the diameter is significantly less. For example in the preferred embodiment end 12 has a diameter of 14 French OD 0.184 inch with a wall thickness of approximately 0.030 inch. The body section extending from the weighted end beyond the taper shown, is about 9 French with an outer diameter of 0.118 inch and an ID of about 0.079 inch. The overall length of the device is a hundred and fifteen centimeters with the weighted end having a length of about 5 centimeters. Four or more openings such as 17 can be used if desired.

The material of the wall is preferably a flexible plastic or rubber tube such that thin-walled devices can be made of small diameter. A problem arises because such devices would tend to curl or coil rather than be stretched out by gravity when passed into the body. Thus weights are used.

Figure 2:
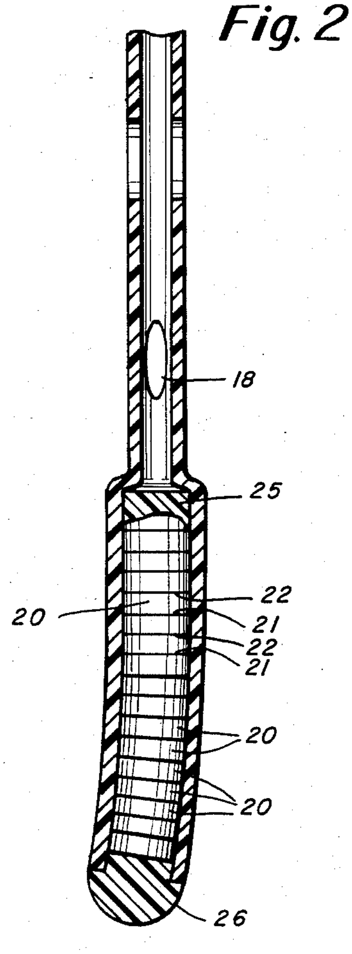
FIG. 2 is an enlarged cross-sectional view thereof taken through line 2—2.

The weighted end section 12 carries within it a plurality of sixteen metal disks 20 each preferably substantially identical to each other. In some cases, the disks can vary in size. It is preferred that each disk have substantially equal diameter and sliding contact faces at edges 21, 22 thereof. These planar contact faces of adjacent disks allow the disks to slide with respect to each other when the tip is bent as shown in FIG. 2. Yet, the disks conform to a high bulk density even when bent slightly by forces within the body. The bulk density is higher than if beads were used or other metallic forms. Preferably the bulk density (solid per unit volume) is at least 70% and the specific gravity is higher than 13.6. Metals such as tungsten, tantalum are preferred for use. Other metals such as platinum having specific gravities above that of mercury or of substantial weight can also be used.

Preferably the length to diameter of the small disks should be in a ratio of 1:1 or less. That is the length should be shorter than the diameter to provide for adequate flexibility of the device. The material of the plastic tube is flexed enough so that the entire length of the weight can be shaped and flexible. The elongation of the plastic or rubber material is sufficient to allow a relatively tight radius of curvature of the entire weight without permanent rupture or deformation of the weighted portion of the tube. Silicone rubber or latex rubber are materials which are preferred for use to meet this specification.

The weights can be assembled in axial alignment with each other and placed into the tube after a plug such as 25 is first adhered in place. An end plug 26 of resilient material can be used to seal the weights in place. Conventional adhesives can be used in the sealing operation.

In the preferred embodiment, sixteen tungsten disks are used with an overall axial length of 4 centimeters with the beads 25 and 26 being of RTV silicone medical grade. The diameter of the disk is such as to be snugly received within the tube. The weights provide sufficient weight to straighten and advance the feeding tube when placed in the body yet allows conformance to various contours of the body when necessary during introduction to the body and thereafter.

A radiopaque stripe 30 is provided which can be detected from outside the body. In some cases, the material of the tube 11 is itself radioopaque to enable an X-ray to find the position of the tube in the body.

While a specific embodiment of this invention has been shown and described, many variations are possible. For example, the specific configuration of the disks can vary greatly. Other shapes can be used and they need not be circular. Similarly the facing surfaces need not be at right angles to central axes of the disks. In some cases the disks can be separated slightly as by thin plastic disks or other forms. In all cases, the metallic disks provide for at least 70% bulk density with sliding surfaces that enable deformation as required. The disks may extend beyond the outer diameter of the tube in some embodiments. For example, the disks can be of larger diameter than the tube and force fit into place to maintain them in position. It is only necessary that a substantial weight be provided while retaining flexibility in devices of this type and with the use preferably of non-toxic material. In some cases, the tube need not be a hollow tube but can in fact be a solid rod.

I claim:

1. A rod-shaped medical device for use in the body and having a flexible weighted portion of greater density than adjacent portions thereof, said weighted portion having specific gravity of about 13.6, said weighted portion comprising:

a tubular body having a closed distal end, an inner wall surface, and an outer wall surface having diameter substantially no more than about one-half inch, said tubular body formed of resilient, yieldable material selected from the class consisting of silicone rubber, and other synthetic and natural rubbers, and, disposed within said tubular body, a multiplicity of disc-form weight elements in stack-like array, said weight elements sized and constructed to occupy substantially the entire volume of said tubular body in said weighted portion, said weight elements having annular surfaces disposed in close proximity to the inner wall surface of said tubular body, and flat surfaces lying generally perpendicular to the coincident local axes of the array and said tubular body, with mating flat surfaces of successive weight elements being substantially parallel, said mating flat surfaces constructed to slide yieldably upon each other in response to force applied to said tubular body to provide flexibility to said weighted portion.

2. The medical device of claim 1 wherein said weight elements are formed of tungsten or tantalum, and the bulk density of said weight elements in said tubular body is at least about 70%.

3. A medical device in accordance with claim 1 wherein said weighted portion comprises a plurality of mating metallic disks.

* * * * *